US009757526B2

(12) United States Patent
Iwase et al.

(10) Patent No.: US 9,757,526 B2
(45) Date of Patent: Sep. 12, 2017

(54) DRUG ADMINISTRATION INSTRUMENT

(71) Applicant: Terumo Kabushiki Kaisha, Tokyo (JP)

(72) Inventors: Yoichiro Iwase, Kanagawa (JP);
Junichi Ogawa, Yamanashi (JP);
Kouichi Tachikawa, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 137 days.

(21) Appl. No.: 14/661,871

(22) Filed: Mar. 18, 2015

(65) Prior Publication Data

US 2015/0190585 A1  Jul. 9, 2015

Related U.S. Application Data

(63) Continuation of application No. PCT/JP2012/074233, filed on Sep. 21, 2012.

(51) Int. Cl.
*A61M 5/32* (2006.01)
*A61M 5/178* (2006.01)
(Continued)

(52) U.S. Cl.
CPC .......... *A61M 5/3202* (2013.01); *A61M 5/178* (2013.01); *A61M 5/3129* (2013.01);
(Continued)

(58) Field of Classification Search
CPC .............. A61M 5/31511; A61M 5/344; A61M 5/31505; A61M 5/3202; A61M 2005/3206
(Continued)

(56) References Cited

U.S. PATENT DOCUMENTS 5,328,485 A 7/1994 Moreno et al.
6,638,255 B1 * 10/2003 Weber ................ A61M 5/3129
604/181

(Continued)

FOREIGN PATENT DOCUMENTS

DE   299 12 965 U1   9/1999
EP   1 291 030 A1    3/2003
(Continued)

OTHER PUBLICATIONS

The Extended European Search Report issued in Application No. 12884905.6 dated Mar. 31, 2016.
(Continued)

*Primary Examiner* — Gerald Landry, II
(74) *Attorney, Agent, or Firm* — Foley & Lardner LLP

(57) ABSTRACT

A drug administration instrument including a syringe including: a tubular surrounding periphery portion forming a drug chamber configured to store a drug; a discharge part disposed at a first axial end of the surrounding periphery portion; and a flange portion disposed at a second axial end of the surrounding periphery portion; and a sheath member having a tubular shape, surrounding an outer circumference of the surrounding periphery portion of the syringe, and holding the syringe. The sheath member includes a fitting part configured to support at least one of the surrounding periphery portion and the discharge part of the syringe.

15 Claims, 4 Drawing Sheets

(51) Int. Cl.
*A61M 5/315* (2006.01)
*A61M 5/34* (2006.01)
*A61M 5/31* (2006.01)

(52) U.S. Cl.
CPC ....... *A61M 5/31511* (2013.01); *A61M 5/3137* (2013.01); *A61M 5/344* (2013.01); *A61M 5/347* (2013.01); *A61M 2005/3104* (2013.01)

(58) Field of Classification Search
USPC .................. 604/187, 192, 195, 198, 232
See application file for complete search history.

(56) References Cited

U.S. PATENT DOCUMENTS

| | | | | |
|---|---|---|---|---|
| 2005/0148931 | A1* | 7/2005 | Juhasz | A61M 5/3232 604/110 |
| 2005/0203466 | A1* | 9/2005 | Hommann | A61M 5/2033 604/240 |
| 2005/0277892 | A1* | 12/2005 | Chen | A61M 5/3202 604/192 |
| 2005/0277893 | A1* | 12/2005 | Liversidge | A61M 5/31501 604/198 |
| 2010/0081998 | A1 | 4/2010 | Brand | |
| 2011/0226646 | A1* | 9/2011 | Wyrick | A61M 5/002 206/365 |
| 2012/0220951 | A1 | 8/2012 | Kakiuchi | |
| 2013/0079729 | A1 | 3/2013 | Yokota et al. | |
| 2013/0211339 | A1* | 8/2013 | Roberts | A61M 5/3202 604/198 |
| 2013/0211340 | A1* | 8/2013 | Helmer | A61M 5/3276 604/198 |
| 2013/0281938 | A1* | 10/2013 | Ekman | A61M 5/20 604/198 |
| 2013/0345630 | A1* | 12/2013 | Jiang | A61M 5/31511 604/110 |

FOREIGN PATENT DOCUMENTS

| | | |
|---|---|---|
| EP | 1 530 979 A1 | 5/2005 |
| EP | 2 468 343 A1 | 6/2012 |
| FR | 2 899 482 A1 | 10/2007 |
| GB | 2484490 A | 4/2012 |
| JP | 2003-505160 A | 2/2003 |
| JP | 2009-533124 A | 9/2009 |
| JP | 2011-212185 A | 10/2011 |
| JP | 2012-508058 A | 4/2012 |
| WO | WO-2006/072135 A1 | 7/2006 |
| WO | WO-2007/132353 A2 | 11/2007 |
| WO | WO-2010/053570 A1 | 5/2010 |
| WO | WO-2011/055782 A1 | 5/2011 |

OTHER PUBLICATIONS

International Search Report issued in International Patent Application No. PCT/JP2012/074233 mailed Dec. 4, 2012.

* cited by examiner

DRUG ADMINISTRATION INSTRUMENT

CROSS-REFERENCE TO RELATED APPLICATIONS

This application is a continuation application filed under 35 U.S.C. 111(a) claiming the benefit under 35 U.S.C. §§120 and 365(c) of PCT International Application No. PCT/JP2012/074233 filed on Sep. 21, 2012, the entire content of which is hereby incorporated by reference in its entirety.

BACKGROUND

Technical Field

The present disclosure relates to a drug administration instrument for administering drug into a body, various medical devices, infusion containers, and the like.

Background Art

In recent years, prefilled syringes whose syringe is prefilled with a medicinal fluid (drug administration instruments) have been used widely. In administering medicinal fluid using such prefilled syringe, there is no need to draw the medicinal fluid from a vial (bottle) into the syringe, whereby time required for administration can be saved.

In general, a prefilled syringe includes a stationary part and a plunger. To administer a drug into the body using a prefilled syringe, the plunger is operated so that the drug in a liquid chamber in the stationary part is released in vivo via a needle connected to the barrel end of the stationary part.

In administering a relatively small dose of the drug, a compact prefilled syringe having a small liquid chamber is used. For example, to insert the needle perpendicular to the skin and inject the drug into the upper layer of the skin, a considerable pressure to the injection site is required, and the prefilled syringe must be firmly held against the skin in order to prevent leakage of the drug. However, conventional compact prefilled syringes do not have a suitable structure to remain firmly held against the skin, making them difficult to use. Another challenge for users is that, even though a compact prefilled syringe having a small liquid quality is used for administering a small amount of the drug on the order of 0.05-0.5 mL taking into account drug delivery to the upper layer of the skin, it is difficult to keep track of the movement of the plunger. Thus, there is a need for an injection technique in which a user is able to know when the injection is completed.

A drug administration instrument with increased operability is described in JP 2011-212185 A, for example. The drug administration instrument described in JP 2011-212185 A has a barrel having a liquid chamber for storing a drug, a pusher to be passed inside the barrel, a grip, and a connecting part. The pusher includes a rod-like plunger and a gasket. The grip is disposed along an outer circumference of the barrel, and the connecting part is formed between the barrel and an end of the grip. In the drug administration instrument described in JP 2011-212185 A, because the grip is disposed along the outer circumference of the barrel, the grip is easy to hold, whereby a user can apply more force to the pusher.

However, the grip and the barrel for the drug administration instrument described in JP 2011-212185 A are integrally molded, and the barrel has a dual-tube structure partially. As a result, for the drug administration instrument described in JP 2011-212185 A, it is necessary to additionally manufacture a syringe, and the structure of a die for molding the syringe is complicated.

Because the syringe of a prefilled syringe is prefilled with a drug, such prefilled syringe requires a drug filling process. For example, in the case of injection into an upper layer of the skin, a typical dose is on the order of 0.03-0.5 mL. In general, a versatile high-speed drug filling machine is used for filling the syringes with the drug. However, for the drug administration instrument described in JP 2011-212185 A, such a versatile high-speed drug filling machine is not usable because of the unique shape of the syringe. Therefore, modification of the high-speed drug filling machine may be necessary and/or the drug filling efficiency is lowered.

SUMMARY OF INVENTION

One objective of certain embodiments of the present invention is to provide a drug administration instrument that does not require modification of a versatile high-speed drug filling machine or does not lower the drug filling efficiency, yet aims to improve operability with a simple configuration.

According to one embodiment, a drug administration instrument includes a syringe and a sheath member.

The syringe has a tubular surrounding periphery forming a drug chamber storing a drug, a discharge part disposed at one end axially of the surrounding periphery, and a flange portion disposed at the other end axially of the surrounding periphery.

The sheath member is tubular, surrounding an outer circumference of the surrounding periphery and an outer circumference of a tip member and holding the syringe. The sheath member has a fitting part that supports the surrounding periphery and/or the discharge part of the syringe.

In one aspect, the sheath member is attached to a syringe, thereby enlarging the diameter of the compact syringe having a small liquid chamber, thus enabling improvement of operability with a simple configuration. Furthermore, because a syringe of general shape is usable, use of versatile high-speed drug filling machine is permitted.

DETAILED DESCRIPTION

In the following, an embodying example of a drug administration instrument of the present invention will be described with reference to FIGS. 1 to 4. It is noted that like reference signs designate like components throughout the drawings. It is also noted that the present invention is not limited by the following embodiment.

The description will be provided below in the following sequence.

Embodying Example
Configuration of Drug Administration Instrument
Assembly of Drug Administration Instrument
Embodying Example
Configuration of Drug Administration Instrument First, the configuration of an embodiment of a drug administration instrument of the present invention (hereinafter, referred to as "the example") will be described with reference to FIGS. 1 to 4.

Figure 1:
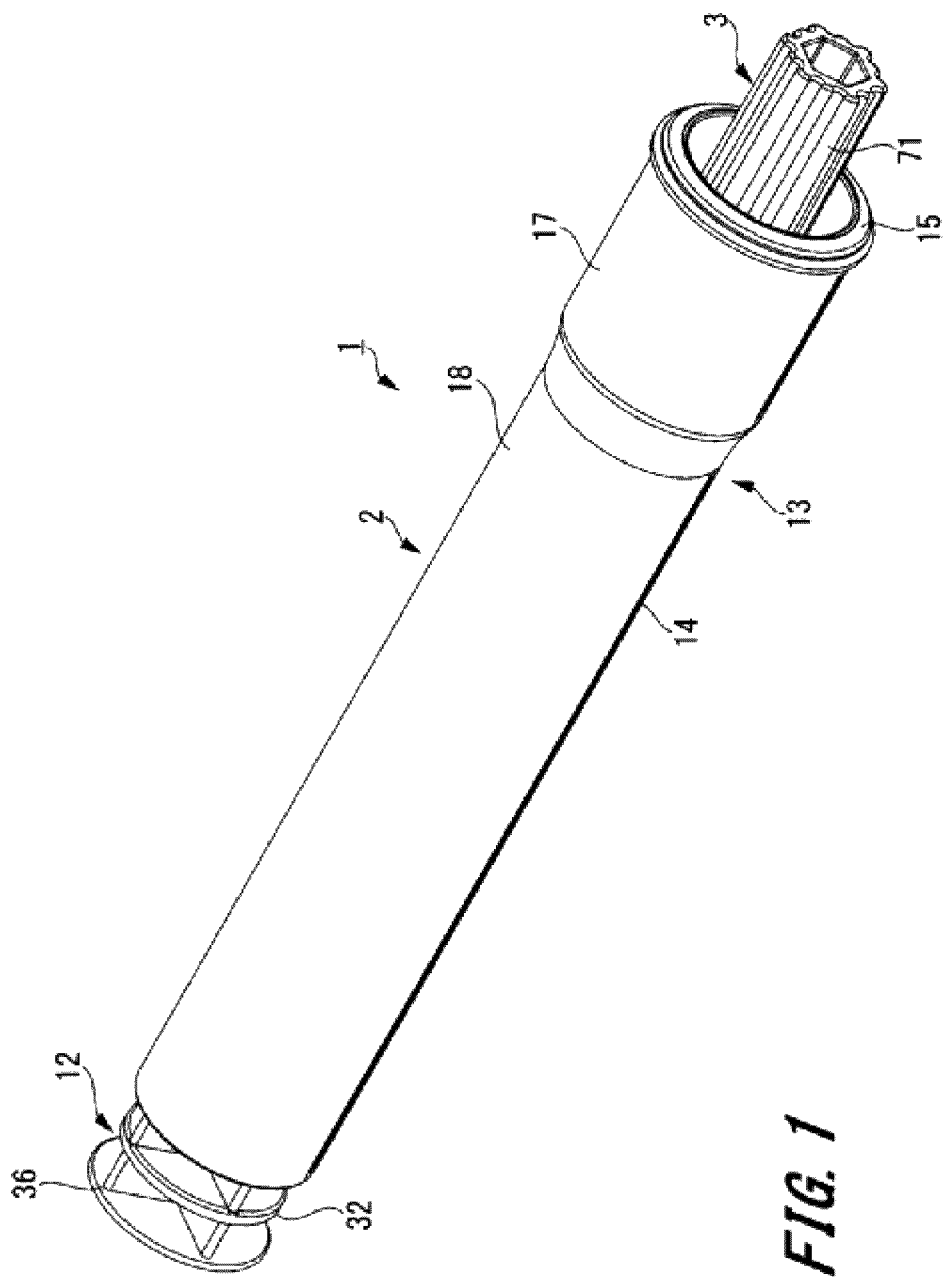
FIG. 1 is a perspective view showing an embodying example of a drug administration instrument of the present invention.
Figure 2:
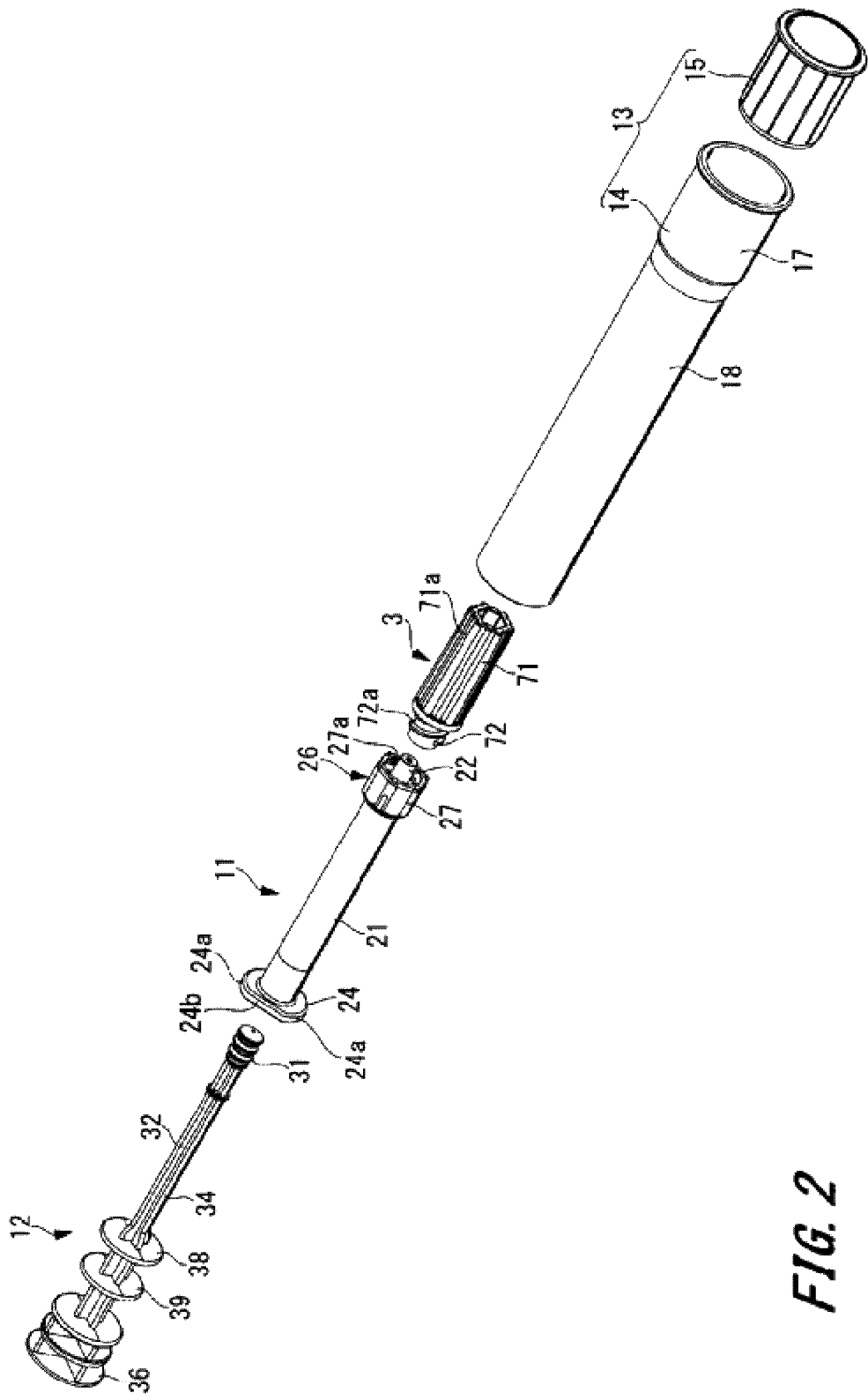
FIG. 2 is an exploded perspective view showing the embodying example of a drug administration instrument of the present invention.
Figure 3:
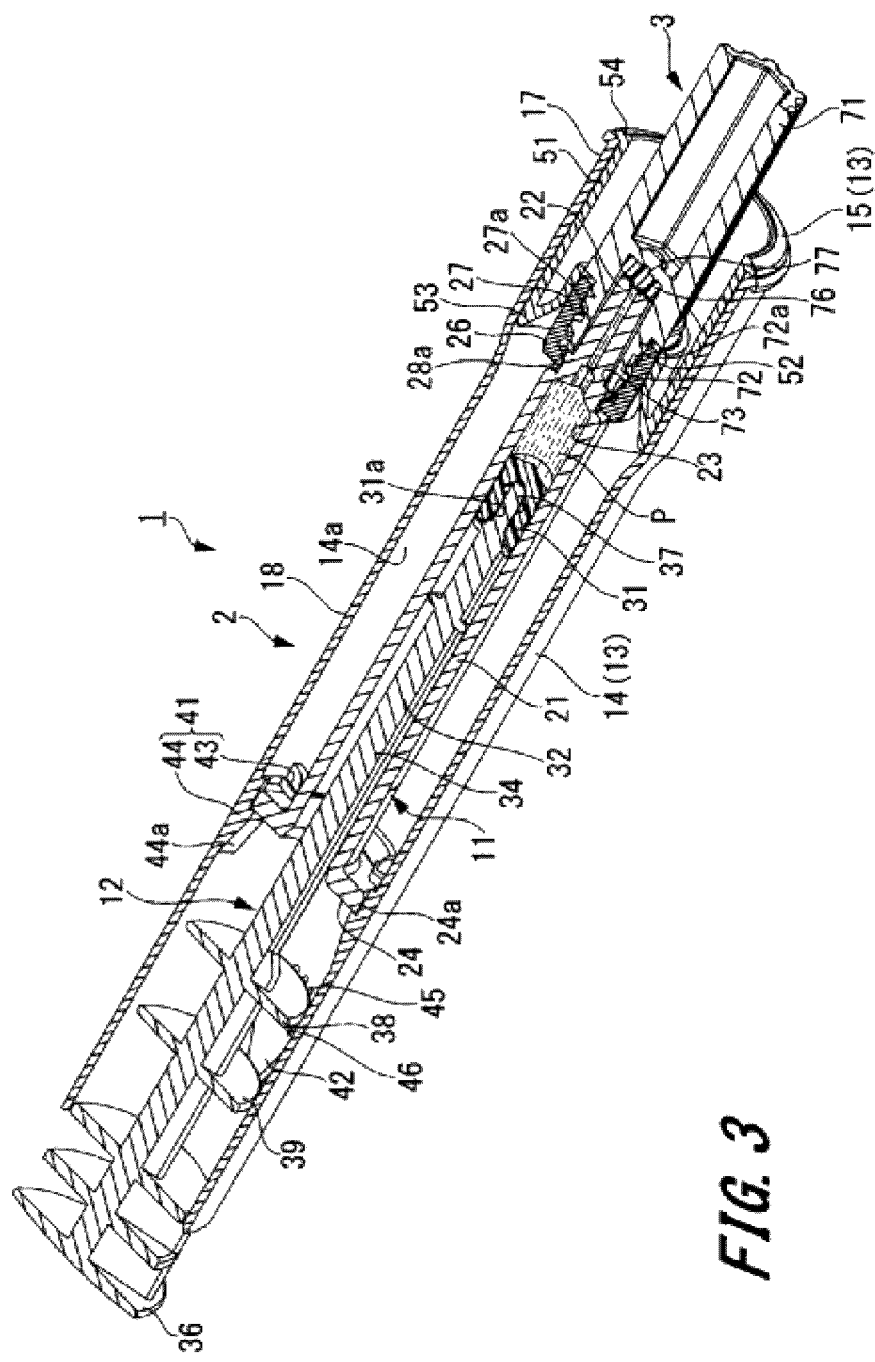
FIG. 3 is a cross-sectional view showing the embodying example of a drug administration instrument of the present invention.

FIG. 1 is a perspective view showing a drug administration instrument of the example. FIG. 2 is an exploded perspective view of an administration instrument body in accordance with the drug administration instrument of the example. FIG. 3 is a cross-sectional view showing the drug administration instrument of the example.

As shown in FIG. 1, a drug administration instrument 1 includes an administration instrument body 2 and a cap 3 that is detachably attached to the administration instrument body 2. As shown in FIG. 2, the administration instrument body 2 has a syringe 11, a pusher member 12, and a sheath member 13 that is attached to the syringe 11.

Syringe

The syringe 11 is a prefilled syringe that has been prefilled with a drug P (see FIG. 3). The syringe 11 has a surrounding periphery 21 that is substantially cylindrical and a discharge part 22 disposed at one end of the surrounding periphery 21.

As shown in FIG. 3, a liquid chamber 23 for storing the drug P is disposed inside the surrounding periphery 21. The diameter of the surrounding periphery 21 is suitably set depending on the application and/or the capacity for the drug to be stored in the liquid chamber 23. For example, for a capacity of 0.5 mL of drug to be stored using a versatile high-speed drug filling machine, a preferable setting of the outer diameter of the surrounding periphery 21 is 6.8-8.2 mm. For a capacity of 1 mL, a preferable setting of the outer diameter of the surrounding periphery 21 is 8.1-9.4 mm.

Examples of the drug solution P include, but are not limited to, various prophylactic vaccines for infections such as influenza. Examples of drug P other than vaccines include: saccharide infusion solutions such as glucose; electrolyte regulating infusion solutions such as sodium chloride and potassium lactate; vitamins; antibiotic infusion solutions; contrast media; steroids; protease inhibitors; fat emulsions; anticancer agents; anesthetic; heparin calcium; and antibody preparations.

At the other end of the surrounding periphery 21, a flange portion 24 is provided. The flange portion 24 protrudes radially outwardly from an outer circumferential surface at the other end of the surrounding periphery 21, and the flange portion 24 has an outer circumference with a substantially elliptic shape. The outer circumferential shape of the flange portion 24 is formed by opposing two arc-shaped sides 24a and opposing two straight sides 24b continuous to the arc-shaped sides 24a. The two arc-shaped sides 24a engage an engagement section 41 (to be described later) of a tubular body 14 included in the sheath member 13. The diameter of a circle formed with the two arc-shaped sides 24a of the flange portion 24 is set to be 13-19 mm, for example.

The axial length of the surrounding periphery 21 is set within a range of 47-60 mm, for example. When the cap 3 (to be described later) is attached, the length from the flange portion 24 to the tip of the cap 3 is set within a range of 79-92 mm, for example.

The discharge part 22 is continuous to the one end of the surrounding periphery 21 and is substantially cylindrical and coaxial with the surrounding periphery 21. The discharge part 22 has a tapered shape where its diameter continuously decreases toward its tip away from the surrounding periphery 21. A lumen of the discharge part 22 is in communication with a lumen of the surrounding periphery 21.

A luer lock 26 as an example of a tip member that is connected to the discharge part 22. The luer lock 26 has a tube 27 that is substantially cylindrical and coaxial with the discharge part 22 and a fitting part 28 provided at an end of the tube 27 at the side of the surrounding periphery 21. The outer diameter of the tube 27 is larger than that of the surrounding periphery 21, and a gap of a predetermined distance is formed between an inner circumferential surface of the tube 27 and an outer circumferential surface of the discharge part 22. The inner circumferential surface of the tube 27 is provided with an internal thread 27a.

The fitting part 28 includes a plurality of protrusions 28a protruding radially and inwardly from the inner circumferential surface of the tube 27. The plurality of protrusions forming the fitting part 28 is disposed circumferentially of the tube 27 at suitable intervals from one another. The fitting part 28 is fit to a proximal section of the discharge part 22, which is an end of the discharge part 22, at the side of the surrounding periphery 21.

The tip member attached to the discharge part 22 is not limited to the luer lock 26, and various other members can be employed, such as a safety member for a higher level of safety in drug administration using the drug administration instrument 1.

Materials for the syringe 11 can include various types of resins, for example, polyvinyl chloride, polyethylene, polypropylene, cyclic polyolefin, polystyrene, poly-(4-methylpentene-1), polycarbonate, acrylic resin, acrylonitrile-butadiene-styrene copolymer, polyester such as polyethylene terephthalate, butadiene-styrene copolymer, and polyamide (for example, nylon 6, nylon 6/6, nylon 6/10, and nylon 12). Among these, resins like polypropylene, cyclic polyolefin, polyester, and poly-(4-methylpentene-1) are preferable for the ease of molding. It should be noted that the preferable materials for the syringe 11 are substantially transparent for ensuring the visibility of the inside.

A needle holding member is attached to the discharge part 22 of the syringe 11, for example. The needle holding member includes a needle tube and a needle hub for holding the needle tube. The needle hub may be directly attached to the discharge part 22, and is attached to the syringe 11 by screwing onto the luer lock 26. Once the needle holding member is attached to the discharge part 22, a lumen of the needle tube and the inside of the discharge part 22 become in communication with each other in a liquid tight manner.

The drug administration instrument 1 is not limited to such a type that is attached to the needle holding member for use. The drug administration instrument 1 may be used in a manner where the discharge part 22 thereof is connected to a connector (female luer) provided on a medical tube, for example.

Pusher Member

The pusher member 12 has a gasket 31 movably disposed in the surrounding periphery 21 of the syringe 11 and a plunger 32 connected to the gasket 31. Operation of the pusher member 12 results in discharge of the drug P stored in the syringe 11.

The gasket 31 is substantially cylindrical. The gasket 31 is passed along the inner circumferential surface of the surrounding periphery 21 of the syringe 11 in a liquid tight manner. As shown in FIG. 3, the gasket 31 divides the space in the surrounding periphery 21 in two. One of the divided sections located at the side of the discharge part 22 relative to the gasket 31 in the surrounding periphery 21 as well as the space within the discharge part 22 form the liquid chamber 23 that is filled with the drug P. The other of the divided sections located at the side of the other end of the surrounding periphery 21 relative to the gasket 31 is disposed with a plunger body 34 (to be described later) of the plunger 32.

One end of the gasket 31 has a tapered shape where its diameter continuously decreases toward its tip. This tapered shape corresponds to the shape of an inner surface at the one end of the surrounding periphery 21. Thus, when the gasket 31 is moved to the one end of the surrounding periphery 21, one end of the gasket 31 comes in contact therewith such that no gap is generated at the inner surface at the one end of the surrounding periphery 21.

In an end face at the other end of the gasket 31, a fitting hole 31*a* is provided. In the inner surface of the gasket 31 forming the fitting hole 31*a*, a convex-and-concave section or an internal thread is formed, onto which a connecting protrusion 37 (to be described later) of the plunger body 34 is screwed, for example.

Materials for the gasket 31, without limitation, are preferably composed of resilient materials in order to obtain a good level of liquid tightness in relation to the surrounding periphery 21. Such resilient materials can include, for example, various rubber materials such as natural rubber, isobutylene rubber, and silicone rubber; various thermoplastic elastomers such as olefin-base and styrene-base ones; and combinations thereof.

The plunger 32 has the plunger body 34 connected to the gasket 31 and an operating section 36 for operating the plunger body 34. Resins that have been listed as materials for the syringe 11 may be used as materials for the plunger 32.

The plunger body 34 is substantially cylindrical. At one end of the plunger body 34, the connecting protrusion 37 is provided. The connecting protrusion 37 is substantially cylindrical and coaxial with the plunger body 34 and is connected to the gasket 31 by press fitting. In an outer circumferential surface of the connecting protrusion 37, an external thread may be formed so as to be screwed onto the internal thread of the gasket 31.

It is noted that, the connection method between the connecting protrusion 37 and the gasket 31 is not limited to the press fitting of the connecting protrusion 37 but also other methods, such as screwing and adhesive bonding, may be adopted.

The operating section 36 is provided at the other end of the plunger body 34. The operating section 36 is substantially disc-like. When a user pushes the operating section 36 during use of the drug administration instrument 1, the gasket 31 provided at the tip of the plunger 32 is moved through the surrounding periphery 21 of the syringe 11.

At the side of the other end of the plunger body 34, an antidislodgement part 38 and a click-feeling generator 39 are provided. The antidislodgement part 38 and the click-feeling generator 39 are provided at one side axially of the plunger body 34 relative to the operating section 36. The antidislodgement part 38 and the click-feeling generator 39 are substantially disc-like. It is noted that, the shapes of the antidislodgement part 38 and the click-feeling generator 39 are not limited to the substantially disc-like shape but other shapes may be adopted, such as a substantially elliptic shape, substantially rectangular shape, and the like.

Sheath Member

The sheath member 13 includes the tubular body 14 and a fitting member 15. The tubular body 14 is substantially tubular, surrounding the outer circumferential surface of the surrounding periphery 21 of the syringe 11 and an outer circumferential surface of the tube 27 of the luer lock 26. The tubular body 14 is adapted so that one side along its axis serves as an attachment section 17 while the other side along its axis serves as a grip 18. The diameter of the grip 18 is set smaller than that of the attachment section 17. The inner diameters of the grip 18 and the attachment section 17 of the tubular body 14 are set larger than the outer diameters of the surrounding periphery 21 and the tube 27.

Figure 4:
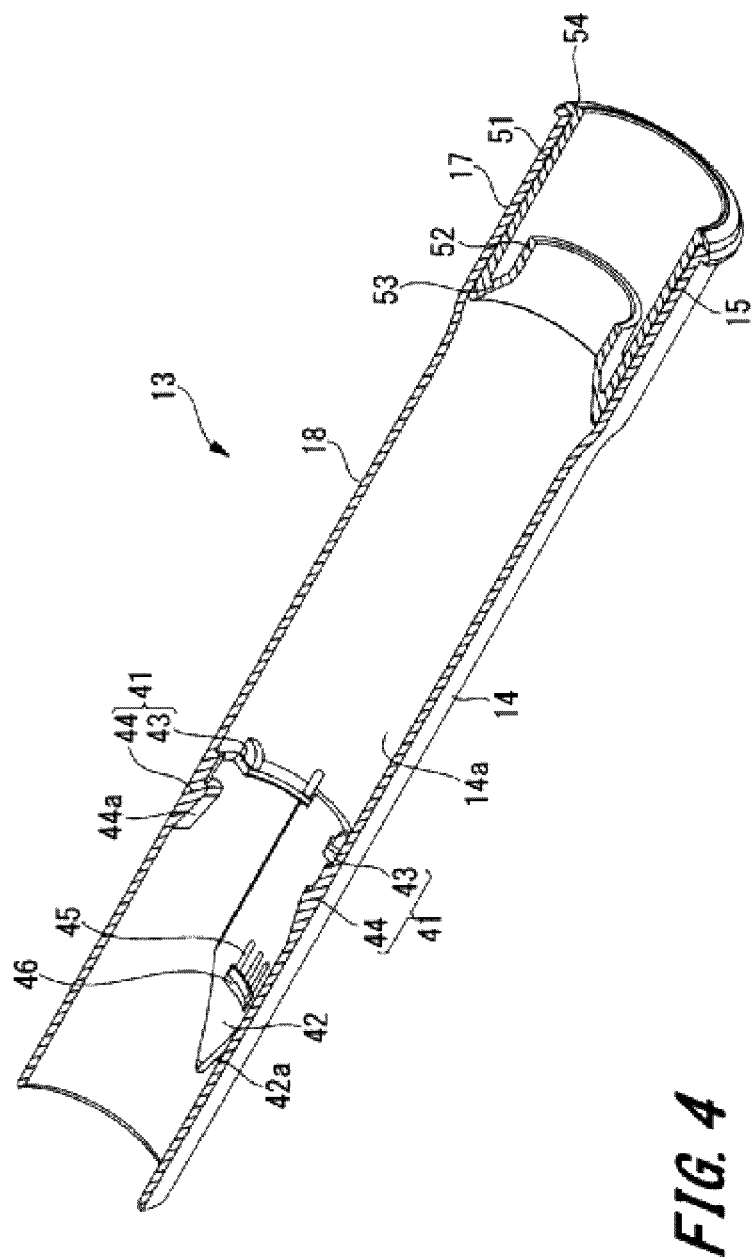
FIG. 4 is a cross-sectional view showing a sheath member according to the embodying example of a drug administration instrument of the present invention.

FIG. 4 is a cross-sectional view showing the sheath member 13.

As shown in FIG. 4, to the one side axially of the tubular body 14, i.e., the attachment section 17, the fitting member 15 is attached by means of securing technique, for example, press fitting. Further, in about the middle of the tubular body 14, which is an inner wall 14*a* of the grip 18, an engagement section 41 and a guide section 42 are disposed.

The engagement section 41 has a first engagement protrusion 43 and a second engagement protrusion 44. The first engagement protrusion 43 is flange-like and protrudes radially and inwardly from the inner wall 14*a* of the tubular body 14. The second engagement protrusion 44 is provided at the other side axially of the tubular body 14 relative to the first engagement protrusion 43. The second engagement protrusion 44 is substantially rectangular parallelepipedic and has an angled face 44*a*. The angled face 44*a* is beveled toward the other side of the tubular body 14.

The first engagement protrusion 43 and the second engagement protrusion 44 are separated from each other by a thickness of the flange portion 24 along the axis of the tubular body 14. Thus, as shown in FIG. 3, the arc-shaped sides 24*a* of the flange portion 24 fit in between the first engagement protrusion 43 and the second engagement protrusion 44, whereby the engagement section 41 and the flange portion 24 engage with each other.

The guide section 42 is formed at the other side axially of the tubular body 14 relative to the engagement section 41. The guide section 42 is disposed as a raised surface that is raised radially and inwardly from the inner wall 14*a* of the tubular body 14. A guide side 42*a* disposed at the other side axially of the guide section 42 is angled relative to the axis. During assembly of the administration instrument body 2, a chuck member supporting the syringe 11 will slide against the guide side 42*a*.

The guide section 42 of the tubular body 14 is also provided with a plunger support 45 and a convex part 46. The plunger support 45 and the convex part 46 are provided between the guide section 42 and the engagement section 41, where the convex part 46 is disposed at the other side axially relative to the plunger support 45. When the sheath member 13 is attached to the syringe 11, the antidislodgement part 38 of the plunger body 34 is crossing over the convex part 46 to be disposed at the plunger support 45 which supports the antidislodgement part 38. In this way, displacement of the pusher member 12 due to external forces, such as vibration and fall generated during transportation, is prevented. Furthermore, a surface of the convex part 46 at the side of the plunger support 45 abuts against the antidislodgement part 38, thereby preventing the pusher member 12 from being dislodged from the syringe 11.

In drug administration, the user will experience a click feeling as the click-feeling generator 39 of the plunger body 34 crosses over the convex part 46. With this click feeling, the user is notified of completion of the injection and drug administration. The strength of the click feeling generated by the click-feeling generator 39 and the convex part 46 can be adjusted by the settings of the outer diameter of the click-feeling generator 39 and the inner diameter of the tubular body 14 as well as the thickness of the click-feeling generator 39 and the hardness of materials therefor.

The axial length of the tubular body 14 is set as an entire length from the flange portion 24 of the syringe 11 to the discharge part 22, for example, in a range of 70-130 mm. The outer diameter of the grip 18 is set in a range of, for example, 14.2-30 mm.

The fitting member 15 includes a stationary part 51 and a fitting part 52 each having a ring-like shape, and a connecting part 53 interconnecting the stationary part 51 and the fitting part 52. The outer diameter of the stationary part 51 is set almost equal to the inner diameter of the tubular body 14. The stationary part 51 is press fit into a lumen of the tubular body 14. At one end of the stationary part 51, a flange 54 is provided. The flange 54 is radially, outwardly protruded from an outer circumferential surface of the stationary part 51 at the one end thereof. The flange 54 abuts against an end face at the one end axially of the tubular body 14.

The fitting part 52 has a ring-like shape encircling the outer circumferential surface of the tube 27 of the luer lock 26. The fitting part 52 is disposed in the stationary part 51 such that the radial center of the fitting part 52 coincides with that of the stationary part 51. The inner diameter of the fitting part 52 is set substantially equal to the outer diameter of the tube 27 of the luer lock 26. As shown in FIG. 3, the fitting part 52 abuts against the tube 27 of the luer lock 26. Thus, the fitting member 15, via the luer lock 26, supports the tip portion of the syringe 11 at the side of the discharge part 22, that is, the surrounding periphery 21 of the syringe 11 and/or the discharge part 22.

Although the example, as shown in FIG. 3, illustrates a case in which the fitting part 52 is always in contact with the tube 27 of the luer lock 26, this is not intended to be a limitation. For example, there may be a slight gap between the fitting part 52 and the tube 27, such that the fitting part 52 and the tube 27 abut against each other when the syringe 11 or the fitting member 15 is inclined.

The connecting part 53 interconnects the other end of the stationary part 51 and the other end of the fitting part 52. The connecting part 53 has a tapered shape where its diameter continuously decreases toward the fitting part 52 away from the stationary part 51.

Resins that have been listed as materials for the syringe 11 may be used as materials for the sheath member 13. It should be noted that the preferable materials for the sheath member 13 are substantially transparent for ensuring the visibility of the inside.

Cap

As shown in FIG. 3, the cap 3 is substantially cylindrical and bottomed, having a discharge part through hole 73 therein, and the cap 3 has a larger diameter portion 71 forming one end along its axis and a smaller diameter portion 72 forming the other end along its axis. The larger diameter portion 71 has a larger diameter than the smaller diameter portion 72.

In an outer circumferential surface of the larger diameter portion 71, a plurality of ridges 71a is formed, extending along the axis of the cap 3. The ridges 71a are provided so as to increase frictional resistance between the cap 3 and the user's finger when the user removes the cap 3 from the syringe 11. In an outer circumferential surface of the smaller diameter portion 72, an external thread 72a is formed so as to be screwed onto the internal thread 27a in the luer lock 26 of the syringe 11.

The discharge part through hole 73 extends along the axis of the cap 3. One end of the discharge part through hole 73 is opened at an end face of the smaller diameter portion 72 while the other end is located in the middle of the larger diameter portion 71. At the other end of the discharge part through hole 73, a packing 76, made of a substantially cylindrical resilient material (e.g., rubber), is fitted.

At about the center of the packing 76, a packing convex part 77 is protruded along the axis of the cap 3. The packing convex part 77 seals a discharge port of the discharge part 22. In this way, the drug P stored in the liquid chamber 23 is prevented from leaking out of the syringe 11 through the discharge port of the discharge part 22.

To attach the cap 3 to the administration instrument body 2, the discharge part 22 of the syringe 11 is inserted into the discharge part through hole 73 of the cap 3. Now the smaller diameter portion 72 of the cap 3 has been inserted into the tube 27 of the luer lock 26. Then, the cap 3 is rotated in the direction for attachment. As a result, the external thread 72a of the smaller diameter portion 72 is screwed onto the internal thread 27a of the luer lock 26, whereby the packing convex part 77 seals the discharge port of the discharge part 22. Attachment of the cap 3 to the administration instrument body 2 is thus completed.

Assembly of Drug Administration Instrument

Next, assembly of a drug administration instrument 1 will be described.

To assemble the drug administration instrument 1, first, a luer lock 26 is connected to a discharge part 22 of a syringe 11. Here, a fitting part 28 of the luer lock 26 is fitted to and thus fixed to the discharge part 22.

Then, a cap 3 is attached to the luer lock 26 by screwing an external thread 72a of the cap 3 onto an internal thread 27a of the luer lock 26. In this way, a discharge port of the discharge part 22 of the syringe 11 is sealed by a packing 76.

Subsequently, a surrounding periphery 21 of the syringe 11 is filled with a drug P. Then, a gasket 31 of a pusher member 12 and a plunger body 34 connected to the gasket 31 are inserted into the surrounding periphery 21 of the syringe 11 at the other end of the surrounding periphery 21. The gasket 31 and the plunger body 34 are inserted into the surrounding periphery 21 by mechanical stoppering or vacuum stoppering technique, for example.

It is noted that, only the gasket 31 may be inserted into the surrounding periphery 21 initially, and after attaching a sheath member 13 to the syringe 11, the plunger body 34 may be connected to the gasket 31.

Now, the syringe 11 is supported by an unshown chuck member and inserted into a lumen of a tubular body 14 at an opening thereof at the other side axially of the tubular body 14. Arc-shaped sides 24a of a flange portion 24 of the syringe 11 abut against a second engagement protrusion 44 of an engagement section 41 in the tubular body 14. The second engagement protrusion 44 is provided with an angled face 44a. Thus, as the arc-shaped sides 24a of the flange portion 24 abut against the angled face 44a of the second engagement protrusion 44. As the syringe 11 is passing through the tubular body 14, the syringe 11 or the tubular body 14 undergoes an elastic deformation. In this way, the arc-shaped sides 24a cross over the second engagement protrusion 44 and fit in between the second engagement protrusion 44 and a first engagement protrusion 43. Hence, the arc-shaped sides 24a of the flange portion 24 and the engagement section 41 of the tubular body 14 engage with each other.

The chuck member is provided with a slidable section for sliding along a guide side 42a of a guide section 42 disposed on an inner wall 14a of the tubular body 14. Thus, the syringe 11 supported by the chuck member is rotated, guided by the guide section 42, such that swift positioning of the arc-shaped sides 24a in relation to the engagement section 41 is facilitated.

Further, an antidislodgement part 38 of the plunger body 34 is disposed at a plunger support 45, crossing over a convex part 46. In this way, the antidislodgement part 38 is supported by the plunger support 45 as well as abuts against a surface of the convex part 46 at the side of the plunger support 45. Hence, displacement of the pusher member 12 and dislodgement of the pusher member 12 from the syringe 11 due to external forces such as vibration and fall generated during transportation can be prevented.

In this manner, the side of the other end of the syringe 11 along its axis is supported by the tubular body 14. However, in order to facilitate smooth passing of the luer lock 26 attached to the tip of the syringe 11, the inner diameter of the tubular body 14 is set larger than the outer diameters of the tube 27 of the luer lock 26 and the surrounding periphery 21 of the syringe 11. As a result, a gap is formed between the tube 27 at one end axially of the syringe 11 and the inner wall 14a of the tubular body 14, which may cause rattling of the syringe 11 within the tubular body 14, left this way.

Subsequently, a fitting member 15 is inserted into the tubular body 14 in such manner that the connecting part 53 side of the fitting member 15 is first inserted into the tubular body 14 through an opening disposed at one end along the axis of the tubular body 14. The connecting part 53 has a tapered shape. As a result of this, during the insertion of the fitting member 15 into the tubular body 14, the connecting part 53, upon abutting against the tip of the tube 27, guides the tube 27 into a fitting part 52. In this way, the fitting member 15 can be inserted with ease between the tubular body 14 and the tube 27. Now a stationary part 51 of the fitting member 15 has been brought into intimate contact with the inner wall 14a of the tubular body 14, and the fitting part 52 of the fitting member 15, via the tube 27, supports the surrounding periphery 21 and/or the discharge part 22 of the syringe 11. Thus, both axial ends of the syringe 11 are supported by the sheath member 13, and assembly of the drug administration instrument 1 is completed.

Although the example has illustrated a case in which the syringe 11 is inserted into the tubular body 14 and then the fitting member 15 is attached, the fitting member 15 may have been attached to the tubular body 14 before the syringe 11 is inserted into the tubular body 14. The way to fix the fitting member 15 to the tubular body 14 is not limited to press fitting but also other fixing techniques, such as adhesive bonding, engagement, and the like, may be used.

Further, although the example has illustrated a case in which the sheath member 13 includes the tubular body 14 and the fitting member 15 which are separate members, this is not intended as a limitation The tubular body 14 and the fitting member 15 may be molded integrally to form the sheath member 13.

In accordance with the drug administration instrument 1 of the example, the gap between the tube 27 and the inner wall 14a of the tubular body 14 is filled with the fitting member 15; therefore, rattling of the syringe 11 within the tubular body 14 can be prevented. Furthermore, flection or elastic deformation of the connecting part 53 of the fitting member 15 can absorb dimensional deviation of the tube 27, the tubular body 14, and the like, contributing to more effective prevention of rattling of the syringe 11.

Furthermore, by attaching the sheath member 13 to the syringe 11, the diameter of the administration instrument body 2 is enlarged, which makes it easier for a user to hold the administration instrument body 2. This leads to improvement in operability of the pusher member 12. Also, in accordance with the drug administration instrument 1 of the example, the sheath member 13 can be attached to a general syringe with ease without changing the shape of the syringe 11.

In the preceding description, the embodying example of a drug administration instrument of the present invention has been described, including the functional effects thereof. However, it is appreciated that the drug administration instrument of the present invention is not limited to the above embodiment, but various modifications are possible without departing from the general outline of the invention as stated in the claims.

What is claimed is:

1. A drug administration instrument comprising:
    a syringe including:
        a tubular surrounding periphery portion forming a drug chamber configured to store a drug;
        a discharge part disposed at a first axial end of the surrounding periphery portion; and
        a flange portion disposed at a second axial end of the surrounding periphery portion;
    a sheath member having a tubular shape, surrounding an outer circumference of the surrounding periphery portion of the syringe, and the discharge part of the syringe, wherein the sheath member includes a fitting part configured to support at least one of the surrounding periphery portion and the discharge part of the syringe; and
    a tip member located between the sheath member and said at least one of the surrounding periphery portion and the discharge part of the syringe,
    wherein the fitting part supports said at least one of the surrounding periphery portion and the discharge part via the tip member.

2. The drug administration instrument according to claim 1, wherein the sheath member includes an engagement section that engages with the flange portion of the syringe.

3. The drug administration instrument according to claim 1,
    wherein the tip member is attached to the discharge part of the syringe and has an outer diameter larger than that of the surrounding periphery portion.

4. The drug administration instrument according to claim 1, wherein the sheath member comprises:
    a tubular body surrounding an outer circumference of the syringe; and
    a fitting member fixed to a first axial end of the tubular body and including the fitting part.

5. The drug administration instrument according to claim 4, wherein the fitting member includes:
    a ring-like stationary part fixed in a lumen of the tubular body; and
    a connecting part interconnecting the stationary part and the fitting part,
    wherein the fitting part is ring-like and is disposed coaxially with the stationary part.

6. The drug administration instrument according to claim 4,
    wherein the drug administration instrument is configured such that the syringe is insertable into the tubular body in such a manner that a discharge part side of the syringe is insertable into the tubular body through a second axial end of the tubular body,
    wherein the drug administration instrument is configured such that the flange portion and the engagement section are engageable with each other after the syringe is inserted into the tubular body, and wherein the drug administration instrument is configured such that, after the syringe is inserted into the tubular body, the fitting member is press fittable at the first axial end of the tubular body such that the fitting member is disposed between the tubular body and at least one of the surrounding periphery portion and the discharge part.

7. The drug administration instrument according to claim 2, wherein the sheath member includes a guide section configured to guide engagement between the engagement section and the flange portion.

8. The drug administration instrument according to claim 1, wherein the tip member is a luer lock.

9. The drug administration instrument according to claim 1, further comprising:
a pusher member for pushing out the drug stored in the syringe,
wherein the pusher member includes a click-feeling generator configured such that, upon discharge of the drug, the click-feeling generator generates a click feeling by crossing over a convex part disposed in the sheath member.

10. The drug administration instrument according to claim 4, further including:
a tip member attached to the discharge part of the syringe and having an outer diameter larger than that of the surrounding periphery portion,
wherein the fitting part supports at least one of the surrounding periphery portion and the discharge part via the tip member.

11. The drug administration instrument according to claim 10, wherein the fitting member includes:
a ring-like stationary part fixed in a lumen of the tubular body; and
a connecting part interconnecting the stationary part and the fitting part, wherein the fitting part is ring-like and is disposed coaxially with the stationary part.

12. The drug administration instrument according to claim 11,
wherein the drug administration instrument is configured such that the syringe is insertable into the tubular body in such a manner that a discharge part side of the syringe is insertable into the tubular body through a second axial end of the tubular body,
wherein the drug administration instrument is configured such that the flange portion and the engagement section are engageable with each other after the syringe is inserted into the tubular body, and
wherein the drug administration instrument is configured such that, after the syringe is inserted into the tubular body, the fitting member is press fittable at the first axial end of the tubular body such that the fitting member is disposed between the tubular body and at least one of the surrounding periphery portion and the discharge part.

13. The drug administration instrument according to claim 12, wherein the sheath member includes a guide section configured to guide engagement between the engagement section and the flange portion.

14. The drug administration instrument according to claim 13, wherein the tip member is a luer lock.

15. The drug administration instrument according to claim 14, further comprising:
a pusher member for pushing out the drug stored in the syringe,
wherein the pusher member includes a click-feeling generator configured such that, upon discharge of the drug, the click-feeling generator generates a click feeling by crossing over a convex part disposed in the sheath member.

* * * * *